United States Patent [19]

Beahm

[11] Patent Number: 5,302,394
[45] Date of Patent: Apr. 12, 1994

[54] DEXTROMETHORPHAN CONTINUOUS LOZENGE MANUFACTURING PROCESS

[75] Inventor: James S. Beahm, Exton, Pa.
[73] Assignee: McNeil-PPC, Inc., Milltown, N.J.
[21] Appl. No.: 913,260
[22] Filed: Jul. 14, 1992
[51] Int. Cl.⁵ .................................................. A61K 9/68
[52] U.S. Cl. .................................. 424/440; 424/439; 424/441; 424/464; 426/285; 426/660
[58] Field of Search ............... 424/440, 439, 441, 464; 426/660, 285

[56] References Cited

U.S. PATENT DOCUMENTS

| | | | |
|---|---|---|---|
| 3,427,379 | 2/1969 | Barry | 424/440 |
| 4,139,627 | 2/1979 | Lane | 514/315 |
| 4,468,409 | 8/1984 | Metzroth | 426/660 |
| 4,581,232 | 4/1986 | Peters et al. | 424/683 |
| 4,632,821 | 12/1986 | Peters et al. | 424/490 |
| 4,642,231 | 2/1987 | Peters et al. | 424/490 |
| 4,643,892 | 2/1987 | Peters et al. | 424/490 |
| 4,647,459 | 3/1987 | Peters et al. | 424/683 |
| 4,650,663 | 3/1987 | Peters | 514/770 |
| 4,671,953 | 6/1987 | Stanley | 424/440 |
| 4,753,800 | 6/1988 | Mozda | 424/441 |
| 4,980,169 | 12/1990 | Oppenheimer | 424/441 |

OTHER PUBLICATIONS

Handbook of Prescription Drugs, 9th Ed., American Pharmaceutical Association, pp. 202-205, (1990).
H. A. Lieberman, et al., Pharmaceutical Dosage Forms, vol. 1, pp. 342-349, 360-362, 370, 373, 406-409, 411 and 413-415 (1980).

Primary Examiner—Gabrielle Phelan

[57] ABSTRACT

A process for producing a palatable dextromethorphan medicated hard candy lozenges on a continuous system comprising suspending dextromethorphan HBr adsorbate in a liquid suspension and adding this suspension to other candy materials in a novel continuous process.

13 Claims, 2 Drawing Sheets

DEXTROMETHORPHAN CONTINUOUS LOZENGE MANUFACTURING PROCESS

FIELD OF THE INVENTION

This invention relates to a process for producing dextromethorphan medicated hard candy lozenges. More particularly, the process of the invention is capable of producing dextromethorphan lozenges on an efficient continuous system.

BACKGROUND OF THE INVENTION

Dextromethorphan particularly in its hydrobromide salt is a demonstrated safe and effective non-narcotic cough suppressant for the temporary relief of coughing. Dextromethorphan hydrobromide is available in a wide variety of cough and cough/cold medications. Dextromethorphan hydrobromide is available as a sole ingredient in cough medication by itself or with other active ingredients. Dextromethorphan hydrobromide is also available in a cough control lozenge form from various manufacturers which have a dosage of 5.0 milligram of dextromethorphan hydrobromide per lozenge. Such lozenges are in candy form and comprise corn syrup solids and sugar as major ingredients. However, incorporating dextromethorphan hydrobromide into lozenges is highly troublesome because dextromethorphan has a bitter taste an anesthetic mouth-feel and an unpleasant after-taste. In fact it is very difficult to effectively mask the taste of dextromethorphan at concentrations of greater than 2.0 milligrams per lozenge with sweeteners or flavors.

To incorporate more than 2.0 milligrams of dextromethorphan hydrobromide in lozenges the dextromethorphan hydrobromide is generally provided as a 10% adsorbate onto magnesium trisilicate. The adsorbate form provides efficient taste masking to produce an acceptably palatable lozenge form. This adsorbate, which releases the dextromethorphan hydrobromide at the lower pH of the stomach fluids renders the active ingredient almost tasteless in the mouth. Unfortunately, ten times the weight of dextromethorphan hydrobromide adsorbate must be added to achieve an equivalent dosage of dextromethorphan hydrobromide.

Additionally, as reported by David Peters in volume 1 of Pharmaceutical Dosage Forms: Tablets, (3 volume 2nd ed. Herbert A. Lieberman, Leon Lachman and Joseph B. Schwartz. New York: Marcel Dekker, 1989) dextromethorphan hydrobromide adsorbate is insoluble and has a melting point above that of the lozenge's candy base. Therefore, the adsorbate can not be readily incorporated into a candy base. The adsorbate when incorporated into a candy base normally produces a grainy, rough lozenge texture with an unpleasant mouth feel.

To over come this problem the standard solution is to prepare the adsorbate as a granulation of the dextromethorphan hydrobromide adsorbate with either glycerin or propylene glycol. A ratio of one part solvent to three parts dextromethorphan hydrobromide produces a free flowing granulation. Although lozenges made by the above described process can be easily flavored and have a smooth feel, the addition of the adsorbate in this manner limits the amount of dextromethorphan hydrobromide in each lozenge to a dose of 10 milligrams or less. The effective amount of dextromethorphan typically provided in a lozenge is in the range of 5.0 to 7.5 milligram per lozenge unless a large lozenge (4.0 grams) is produced.

Thus, it appears that dextromethorphan hydrobromide cannot readily be incorporated into medicated candy lozenges without special steps being taken. Its successful incorporation into candy bases usually requires a granulation with either glycerin or propylene glycol and an large quantity of inactive material which provides a lozenge with a maximum dosage of 5.0 to 7.5 milligrams per lozenge for an approximately 4.0 gram lozenge product.

The present invention solves these problems by adding the dextromethorphan hydrobromide adsorbate in a liquid suspension into the candy feed prior to the formation of a candy base. The addition of the dextromethorphan adsorbate into the candy feed also dispenses with the need to form a granulation of dextromethorphan adsorbate with glycerin or propylene glycol. These and several other objects and advantages of the present invention will be described in the following sections of this specification.

SUMMARY OF THE INVENTION

It is, therefore, an object of the present invention to provide an alternative manufacturing process for producing a palatable and smooth textured dextromethorphan hydrobromide medicated candy lozenge which is capable of providing at least 2.5 milligram dosage of dextromethorphan hydrobromide in adsorbate form in a lozenge weighing 4 grams or less. It is also an object of the present invention to avoid the granulation of dextromethorphan.

The present invention provides a process for producing dextromethorphan medicated hard candy lozenges comprising the steps of: a) heating a candy making admixture of corn syrup, sucrose syrup and a liquid suspension containing dextromethorphan hydrobromide adsorbate to dehydrate said candy making admixture and produce a dextromethorphan-containing candy mass; b) cooling the candy mass and forming dextromethorphan candy lozenges therefrom.

In another embodiment of the present invention there is also provided a palatable hard candy lozenge weighing less than 4.0 grams and containing in the range of from greater than 10 milligrams to about 20 milligrams of dextromethorphan hydrobromide.

It is to be understood that both the foregoing general and the following detailed description are exemplary and explanatory only and not intended to be restrictive of the invention as claimed.

DETAILED DESCRIPTION OF THE PREFERRED EMBODIMENTS OF THE INVENTION

Reference will now be made in detail to present embodiments of the invention, an example of which is provided in the following example section.

The present invention provides a process for producing a palatable, dextromethorphan medicated hard candy lozenge. The process for making dextromethorphan medicated hard candy lozenges consists generally of mixing at least two different sugar solutions with a liquid suspension of dextromethorphan hydrobromide adsorbate and heating the resultant admixture to dehydrate the solutions. When the desired degree of dehydration is achieved the candy mass is cooled and formed into the desired shapes before it hardens. Flavorings and dyes or coloring agents can be added to the candy while it is still in a liquid state. Typically the flavorings and coloring agents will be added after the candy mass is formed prior to cooling the candy mass.

For manufacturing hard candy lozenges the admixed sugars are generally corn syrup and sucrose syrup. The syrups and the liquid suspension of dextromethorphan hydrobromide adsorbate are admixed in a vessel to form a candy base and then cooked to dehydrate the candy base. For the continuous manufacture of hard candy medicated lozenges the dehydration process generally takes place in two separate steps.

Figure 1:
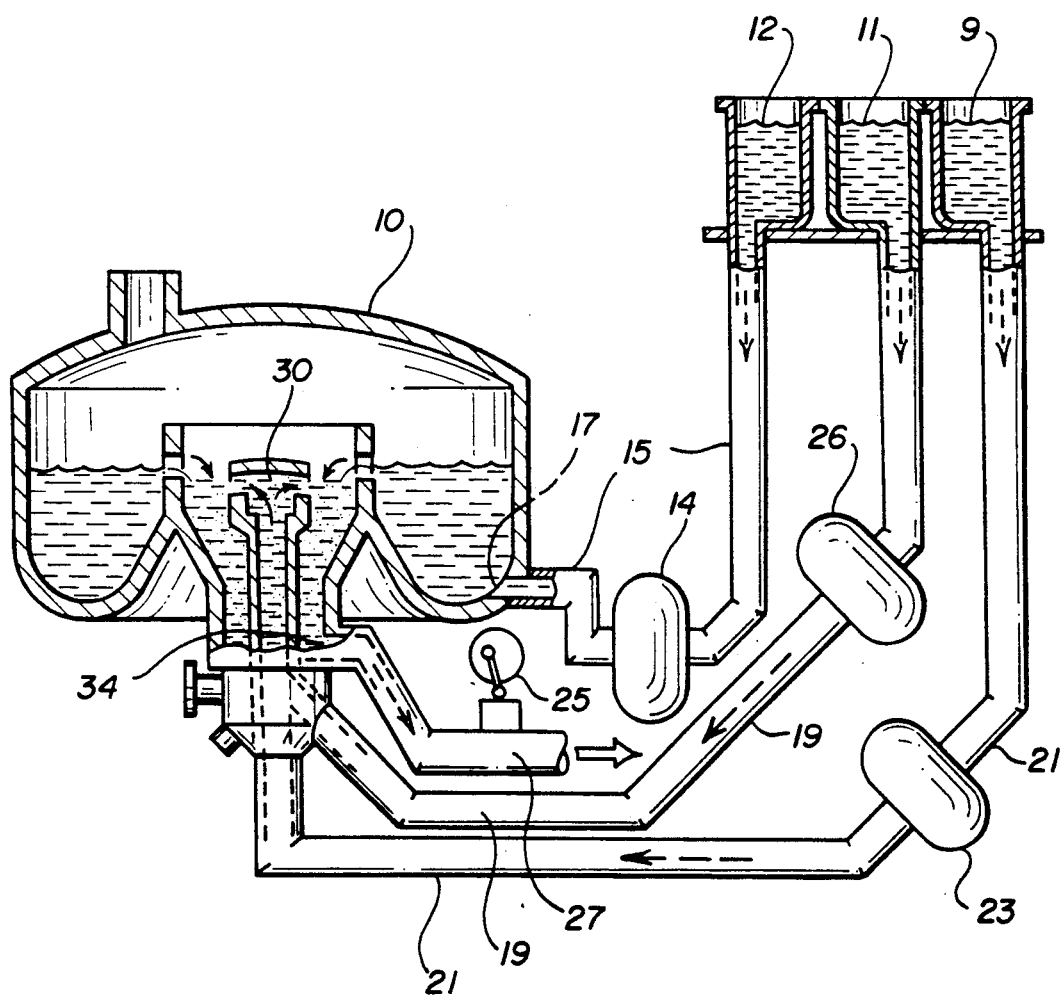
FIG. 1 is a schematic drawing of a Hansella solvomat type precooker.

First the candy base is partially dehydrated in a precooker an example of which is schematically represented in FIG. 1. Then the dehydration is completed in a continuous process cooker an example of which is schematically presented in FIG. 2. As the hard candy mass exits the continuous process cooker, while the candy mass is still a viscous workable liquid, flavors and coloring agents may be admixed into the candy mass. The candy mass then is cooled or tempered and shaped into appropriate lozenge shapes including but not limited to cylindrical, toroidal, octagonal, spherical or biconvex forms.

The dextromethorphan hydrobromide utilized in this process is provided in the form of dextromethorphan hydrobromide adsorbate. The dextromethorphan hydrobromide adsorbate is formed by adsorbing dextromethorphan hydrobromide onto magnesium trisilicate. The adsorbate renders the dextromethorphan hydrobromide almost tasteless but releases the dextromethorphan in the lower pH of the stomach. The adsorbate can be supplied containing in the range of from about 1 percent to about 20 percent dextromethorphan by weight. Preferably the adsorbate will be a 10 percent dextromethorphan hydrobromide adsorbate (10 percent of dextromethorphan hydrobromide by weight adsorbed on 90 percent magnesium trisilicate by weight) provided in a powdered form. Suitable methods for producing this adsorbate are disclosed in U.S. Pat. No. 3,085,942 and more recently U.S. Pat. Nos. 4,632,821, 4,581,232, 4,642,231, 4,647,459, and 4,643,892 (these six patents are hereby incorporated herein by reference). The total amount of dextromethorphan hydrobromide adsorbate per lozenge should be less than 8 percent by weight of the lozenge.

The liquid suspension containing the adsorbate is formed by mixing the dextromethorphan adsorbate in a dry powdered form with a liquid. Alternatively, the dextromethorphan adsorbate may be provided in a liquid based paste and be utilized in that form or mixed with a suitable liquid.

Suitable liquids for suspending dextromethorphan hydrobromide adsorbate may be any liquid solution compatible with the dextromethorphan hydrobromide adsorbate and suitable to be utilized in making hard candy lozenges. As a guideline the liquid should be pharmaceutically acceptable nontoxic liquid which is also nonacidic. The liquid should be nonacidic to avoid possible loss of the taste masking of the dextromethorphan hydrobromide, by its release from the adsorbate which occurs at lower pHs. Suitable suspending liquids including but are not limited to suspending liquids selected from the group consisting of water, aqueous sucrose syrups, corn syrups, sorbitol, polyethylene glycol, propylene glycol, and mixtures thereof. Suitable sucrose syrups for use as a suspending liquid may have a sucrose content of from about 67 to about 80 weight percent sucrose. Similarly, corn syrups used as suspending liquids are recommended to have a solids content of from about 77 to about 82 weight percent solids. The amount of dextromethorphan to liquid suspension should generally be in the range of from about 4 to about 40 percent on a weight percent basis With the total weight of the ingredients equaling 100 percent. The liquid suspension containing the dextromethorphan hydrobromide adsorbate may be constantly agitated such as by stirring means to provide a homogeneous mixture of the dextromethorphan hydrobromide adsorbate and suspending liquid.

The sucrose syrup and corn syrup suitable for manufacturing hard candies are well known in the art (see Pharmaceutical Dosage Forms: Tablets Volume 1, 2nd Ed. editor Herbert A. Lieberman et al. Marcel Dekker, 1989, hereby incorporated by reference). While there may be some variation in the materials utilized in the manufacture of hard candies for lozenges the general starting materials are sucrose syrup (provided in an aqueous solution) with an appropriate corn syrup. The sucrose syrup may be formed in situ or purchased commercially. Generally sucrose is purchased in a solution of approximately 67 percent w/w sucrose (commonly referred to as No. 2 sugar syrup). The corn syrups that may be utilized in hard candy manufacture affect the sweetness and sugar grain size of the resulting lozenges. Generally suitable for hard candy manufacture are low conversion corn syrups (dextrose equivalent, hereinafter, DE of 20-38) regular conversion corn syrup (DE of 38-48) and intermediate conversion corn syrup (DE of 48-58). Presently preferred are corn syrups with a DE of 42-43.

Additionally auxiliary ingredients may be added to the lozenges. Suitable auxiliary medicaments include medicaments selected from the group consisting of the anesthetics: dyclonine, benzyl alcohol, benzocaine, phenol and menthol; the antibacterials: cetylpyridinium and hexylresorcinol; the expectorants: guaifensin and terpin hydrate; the sympathomimetics or decongestants: phenylephrine and phenylpropanolamine; pharmaceutically acceptable salts thereof and mixtures thereof. These medicaments should be provided in amounts effective to provide a therapeutic dosage in lozenge form. Suitable dosage ranges may be found in *Remington's Pharmaceutical Sciences,* 18th edition incorporated herein by reference. Commonly these medicaments are present in a lozenge in the following dosages: dyclonine hydrochloride in the range of from 1 mg to 2 mg, benzyl alcohol in the range of from 1 to 4 percent by weight, benzocaine in the range from 1 mg to 32 mg (preferably in the range of from 1 mg to 10 mg), phenol in the range of from 1 mg to 32.5 mg, menthol in the range of from 0.5 mg to 10 mg, cetylpyridinium chloride in the range of from 0.5 mg to 2.5 mg (preferably in the range of from 2.5 mg to 5 mg), hexylresorcinol in the range of from 0.5 mg to 4 mg (preferably in the range of from 2.4 mg to 4 mg), guaifensin in the range of from 25 mg to 200 mg, terpin hydrate in the range of from 125 mg to 300 mg, phenylephrine hydrochloride in the range of from 10 mg to 20 mg and phenylpropanolamine hydrochloride in the range of from 25 mg to 50 mg. Other suitable auxiliary ingredients include flavoring agents selected from the group consisting of camphor, eucalyptus oil, peppermint oil, capsicum, anise oil, licorice extract, fruit flavors (such as natural and artificial cherry, orange, grape, and lemon flavors) and combination of two or more thereof. The auxiliary ingredients may be added to the candy at any appropriate point in the lozenge making process. Preferably these auxiliary ingredients will be added to the candy mass after it exits the vacuum chamber by a metered dosing pump.

Figure 2:
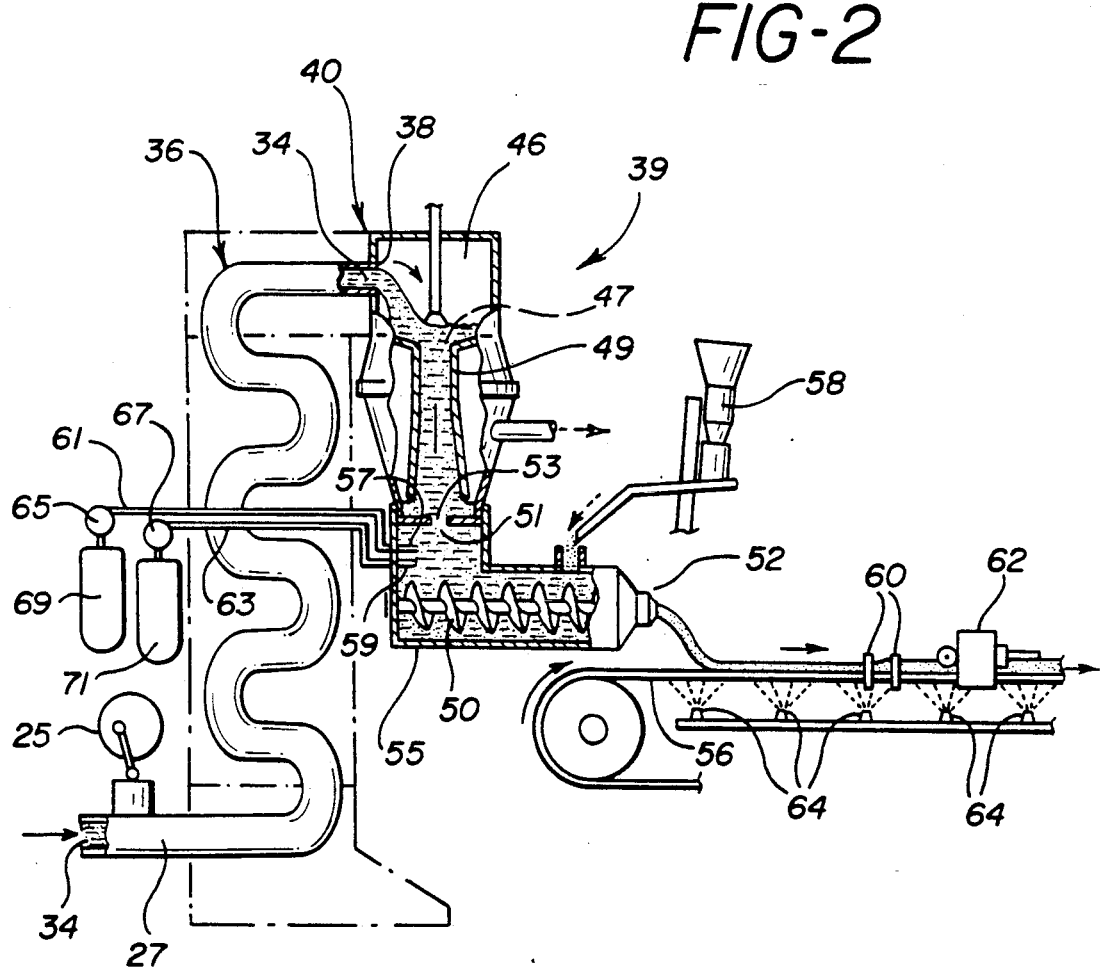
FIG. 2 is a schematic of the continuous process cooker, which illustrates a continuous process in accordance with the present invention.

One embodiment of this invention for the continuous manufacture of medicated hard candy lozenges is illustrated in FIG. 1 and FIG. 2. The first step in making hard candy lozenges shown in FIG. 1 is the mixing of the raw materials in a precooker such as a Hansella precooker. The precooker 10 is supplied with aqueous sugar 12 by pumping the aqueous sucrose solution utilizing a metering pump 14 through a conduit means 15 to inlet port 17. A metered amount of corn syrup is supplied to the precooker utilizing a second metered pump 26, in the direction indicated by the arrows, through conduit means 19 and out inlet port 30. The liquid solution containing the dextromethorphan hydrobromide adsorbate in suspension is supplied to the precooker 10 through the inlet port 30, by a third metered pump 23 via conduit means 21. The mixture of the dextromethorphan hydrobromide adsorbate, sugar syrup (or sucrose syrup) and corn syrup is heated in the precooker to partially dehydrate the mixture and thereby form a candy feed, 34. The temperature to which the mixture is heated should generally be in the range of from about 100° C. to about 120° C. The candy feed is pumped by pump 25 through conduit means 27 into a heat exchanger 36. A heated and/or stirred tank may be placed after pump 25 and before heat exchanger 36 to facilitate controlling the flow of candy feed between the precooker and the heat exchanger. The second step in making hard candy lozenges, shown in FIG. 2, is the cooking of the candy feed. The cooking of the candy feed begins with the introduction of the candy feed into heat exchanger 36. The heat exchanger 36 maintains the candy feed at a temperature sufficient to continue dehydrating said candy feed and thereby forms a candy base. The heat exchanger generally should heat the candy base to a temperature range of from about 130° C. to about 145° C. The candy base is supplied through an outlet port 38, into a continuous process cooker 39 and candy mass maker 40 as provided in FIG. 2.

In FIG. 2, the continuous process cooker and candy mass maker 40 provides a pump 25 for pumping the candy base 34 through the outlet tube 38 into chamber 46 of the cooker unit. The candy base exits chamber 46 by outlet 47. The candy base flow through outlet 47 as a continuous stream into vacuum chamber 49. The vacuum chamber 49 dehydrated the candy base thereby forming a candy mass 51.

The candy mass should have a moisture content in the range of from about 0.5 to about 1.5 percent and preferably a moisture content of about 1 percent by weight after the vacuum dehydration (a higher water content may be acceptable but generally will shorten the shelf life of the lozenges). The candy mass 51 exits the vacuum chamber via outlet 53 as a continuous stream of candy mass. The candy mass flows through outlet 53 into intermediate chamber 55. In intermediate chamber 55 the continuous stream of candy mass may be contacted with auxiliary ingredients such as medicaments, coloring agents and flavoring agents.

In FIG. 2 the coloring agents and flavoring agents are injected into the stream of candy mass through injection ports 57 and 59. The injection ports are connected by conduit means 61 and 63 respectively to metered pumps 65 and 67 respectively. Further conduit means connect the pumps to respective reservoirs 69 and 71 which contain the appropriate coloring agents and flavoring agents. Preferably, the more volatile materials such as some flavorings and other volatile additives will be provided through injection ports 57 and 59 into the intermediate chamber 55 rather than the vacuum chamber 49 which is subject to heat and reduced pressure.

The candy mass 51 then flows out of outlet 52 by the action of a mixing device 50 for delivery onto a steel band conveyor belt 56. An optional powder feeding unit 58 can provide dry powdered constituents to the candy mass. The candy mass 51 is conveyed down the continuous process conveyor belt 56 through a kneading station 60 and is repeatedly subjected to reversing and kneading at plow station 62 for further mixing and shaping. As candy mass 51 moves along the conveyor belt 56 it is subjected to various tempering units which consist of cooling the underside of the conveyor belt with water jets 64.

The temperature of the candy base 51 as it leaves the cooker through outlet 52 is about 130°–135° C. The candy base at this temperature is in a fluid state so that it flows onto the conveyor steel band 56. The width of the outlet sets the width of the candy mass as it is delivered onto the band. Any flavorings and colorings such as may be added by injection ports 57 and 59 into the intermediate chamber 55 or acidulents such as citric acid powder which may be added by powder feeder 58 are mixed and folded into the candy mass by mixing device 50 or by the kneading station 60 and the sets of plows and rollers 62 along the path of the conveyor belt. The candy mass is then provided into a ribbon which may be about 6–10 inches wide. The ribboned candy mass may then be formed into a rope which is cut and shaped into lozenges downstream. The formed lozenges may then be cooled, sized and collected in storage hoppers for distribution and packaging.

The lozenges formed by the process above may contain dextromethorphan hydrobromide in excess of 10 milligrams per lozenge without the lozenge size exceeding 4 grams. The lozenge size may be in the range of from about 2.4 grams to about 4.0 grams. The concentration of dextromethorphan which may be contained in these lozenges will generally be in the range of from about 2.5 to about 20 milligrams of dextromethorphan per lozenge wherein the lozenge is smaller than 4 grams. Thus the lozenges formed by the present process provide a new extra strength dosage lozenge which may contain greater than 10 milligrams per lozenge to about 20 milligrams of dextromethorphan hydrobromide per lozenge and preferably from 11 to about 20 milligrams of dextromethorphan hydrobromide per lozenge. Generally the lozenge size will be in range of from about 2.4 grams to about 4.0 grams per lozenge. The lozenges produced by this process will also have a smooth consistency and good mouth-feel. These lozenges will also not have the bitter taste which is currently associated with lozenges containing over 10 milligrams of dextromethorphan hydrobromide per lozenge.

The lozenges produced in accordance with the continuous process described above have several manufacturing advantages over the batch making process, such as fewer batch records and easier compliance with GMP. These advantages are associated with the elimination of manual mixing in the continuous process. Further, the thoroughness of mixing provided in a continuous process provides a more uniform distribution of ingredients within the lozenges formed by this process. This is particularly important for lozenges containing medicaments produced in accordance with the present invention, which must provide medicaments in a narrow dosage range.

The invention as described above will now be illustrated by use of a specific example of a preferred embodiment in accordance with the invention. The following ingredients and procedures should be read in conjunction with the figures and the description of the figures provided above. The examples provide a specific embodiment of the invention, and are not intended to limit the invention as claimed and amounts and procedures provided therein may be altered to meet certain requirements as would be desired and/or known to those skilled in the art.

EXAMPLE

The following example describes the process of making a 2.5 gram hard candy lozenge containing 100 mg Dextromethorphan HBr Adsorbate on a continuous candy line. The description utilizes a Bosch Continuous Cooker outfitted with an auxiliary ingredient pot with a high capacity Solvomat pump. The example uses but is not limited to a 65:35 ratio of sugar to corn syrup solids respectively. For ease of demonstration, the following example does not account for final water content of lozenge but it is understood that the end product normally will contain from 0.5 to 2.0% moisture. Also, for ease of demonstration, no other ingredients are used in the example. It is understood that other medicaments, acidulents, color, flavor or other pharmaceutically accepted excipients deemed necessary by the formulator could additionally be used in the conventional manner.

1. #2 Sugar Syrup was transferred to a suitable tank. Then the Dextromethorphan HBr Adsorbate was slowly incorporate into the Sugar Syrup to form a creamy smooth, homogeneous suspension using a Homomixer. The suspension was 27.78% w/w Dextromethorphan HBr Adsorbate as follows:

| Suspension Formula: Per Lozenge Wet | |
|---|---|
| Dextromethorphan HBr Adsorbate 10% Micronized | 100.0 mg |
| Sugar Syrup #2, 67 Brix | 260.0 mg |

2. The suspension from step #1 was transferred into the auxiliary feed pot situated before the pre-cooker of the continuous process hard candy assembly The material was kept mixing at this point to avoid any settling of the drug material.

3. The raw material pumps were pre-set to deliver a volumetric ratio of 6.19:2.91:1 of Sugar Syrup #2, Corn Syrup 42/43 and Dextromethorphan HBr Adsorbate suspension respectively.

4. The system was then engaged and the materials were pumped to the steam heated pre-cooker where they were mixed together and cooked down.

5. The material were then expelled from the pre-cooker into the overflow pot where a mixer was set up to keep the ingredients mixing and avoid settling of the suspension.

6. From the overflow pot, the material was pumped to the main cooker (The main cooker temperature is 145° C. with a vacuum of 0.93 Bar) where cookdown was completed and the hot mass flowed through the system in the conventional manner. 2.5 gram lozenges were formed from the candy rope produced by these process. Other ingredients, flavor, color, acidulents and other actives, could be added as appropriate.

7. The lozenges formed weighed 2.5 gram and contains 4% Dextromethorphan HBr Adsorbate (10% DMHBr) and a 65:35 ratio of sugar to corn syrup solids. The unflavored lozenges have a smooth texture and clean sweet taste without noticeable aftertaste from the active.

| Final Lozenge Content Dried Basis | |
|---|---|
| Dextromethorphan HBr Adsorbate 10% Micronized | 100 mg |
| Corn Syrup Solids | 840 mg |
| Sugar | 1560 mg |
| Total | 2500 mg |

The scope of the present invention is not limited by the description, examples and suggested processes described herein and modifications can be made without departing from the spirit of the invention. Applications of the methods and processes of the present invention can be accomplished by any suitable manufacturing method and technique as is presently or prospectively known to those skilled in the art. Thus it is intended that the present application cover the modifications and variations of this invention provided they come within the scope of the appended claims and their equivalents.

What is claimed is:

1. A process for producing dextromethorphan medicated hard candy lozenges comprising the steps of:
   a) heating a candy making admixture of corn syrup, sucrose syrup and a liquid suspension comprising (i) from about 4 to about 40 weight percent of dextromethorphan hydrobromide adsorbate comprising from abut 1 to 20 weight percent dextromethorphan hydrobromide adsorbed onto magnesium trisilicate and (ii) from about 60 to about 96 weight percent of a liquid, to dehydrate said candy making admixture and produce a dextromethorphan-containing candy mass;
   b) cooling the candy mass; and
   c) forming dextromethorphan candy lozenges therefrom.

2. The process of claim 1 wherein the dextromethorphan hydrobromide is present in an amount in the range of from at least 2.5 to about 20 milligram per candy lozenge.

3. The process of claim 1 wherein the liquid is selected from the group consisting of water, sugar syrup, sorbitol, polyethylene glycol, propylene glycol, glycerine, corn syrup and mixtures thereof.

4. A continuous process for producing a hard candy medicated lozenge containing dextromethorphan hydrobromide comprising the sequential steps of:
   a) continuously heating an admixture of candy making corn syrup, sucrose syrup and a liquid suspension comprising (i) from about 4 to about 40 percent of dextromethorphan hydrobromide adsorbate comprising from about 1 to about 20 weight percent dextromethorphan hydrobromide adsorbed onto magnesium trisilicate and (ii) from about 60 to about 96 weight percent of a liquid, in a vessel to partially dehydrate said admixture and thereby form a candy base;

b) continuously removing said candy base from said vessel and;

c) passing said candy base through an apparatus which dehydrates said candy base thereby forming a candy mass thereafter;

d) tempering said candy mass; and e) cooling, cutting and shaping said candy mass to form a medicated lozenge.

5. The process of claim 4 wherein the liquid is selected from the group consisting of water, sugar syrup, sorbitol, polyethylene glycol, propylene glycol, corn syrup and mixtures thereof.

6. The process of claim 4 wherein additionally there is present an effective amount of an auxiliary ingredient selected from the group consisting of: dyclonine, benzyl alcohol, benzocaine, phenol, menthol, cetylpyridinium, hexylresorcinol, guaifensin, terpin hydrate, phenylephrine, phenylpropanolamine, salts thereof and mixtures of two or more thereof.

7. The process of claim 4 wherein the additionally there is present an auxiliary ingredient selected from the group consisting of camphor, eucalyptus oil, peppermint oil, capsicum, anise oil, licorice extract, fruit flavors, and combinations of two or more thereof.

8. The process of claim 4 wherein the lozenge has a total weight of 2.4 to 4 grams and a dextromethorphan content of in the range of from greater than 10 to about 20 milligrams.

9. A process for forming a candy feed comprising mixing corn syrup, sucrose syrup and a liquid suspension comprising (i) from about 4 to about 40 weight percent of dextromethorphan adsorbate comprising from about 1 to about 20 weight percent dextromethorphan hydrobromide adsorbed onto magnesium trisilicate and (ii) from abut 60 to about 96 weight percent of a liquid for processing into a hard candy lozenge.

10. The product produced by the process of claim 1.

11. The product produced by the process of claim 4.

12. The product produced by the process of claim 6.

13. The product produced by the process of claim 7.

* * * * *